United States Patent [19]

Regimand

[11] Patent Number: 4,641,030
[45] Date of Patent: Feb. 3, 1987

[54] APPARATUS AND METHOD FOR DIRECTLY MEASURING THE DENSITY OF A THIN LAYER

[75] Inventor: Ali Regimand, Raleigh, N.C.

[73] Assignee: Troxler Electronic Laboratories, Inc., Research Triangle Park, N.C.

[21] Appl. No.: 681,302

[22] Filed: Dec. 13, 1984

[51] Int. Cl.$^4$ ............................................. G01N 23/00
[52] U.S. Cl. ................................. 250/308; 250/358.1; 378/89
[58] Field of Search ............... 250/308, 358.1; 378/89

[56] References Cited

U.S. PATENT DOCUMENTS 4,525,854  6/1985  Molbert et al. ........................ 378/89

Primary Examiner—Janice A. Howell
Attorney, Agent, or Firm—Bell, Seltzer, Park & Gibson

[57] ABSTRACT

The present invention provides a nuclear radiation backscatter gauge which is capable of directly measuring the density of a thin top layer of material from a composite material comprised of the relatively thin top layer of material applied over an underlying base material. The gauge includes a nuclear radiation source and two radiation detector means so positioned with respect to the source as to form two geometrically differing source-to-detector relationships. A signal processing circuit responds to detected radiation from the two detector means to generate respective signals $D_{G1}$ and $D_{G2}$ representative of the components densities of the top and base layers as measured by the detector means. The density $D_T$ of the thin top layer is then determined by a signal processing means from the relationship $$D_T = \frac{k_2 D_{G1} - k_1 D_{G2}}{k_2 - k_1}$$

wherein $k_1$ and $k_2$ are empirically derived instrument constants.

7 Claims, 4 Drawing Figures

APPARATUS AND METHOD FOR DIRECTLY MEASURING THE DENSITY OF A THIN LAYER

FIELD AND BACKGROUND OF THE INVENTION

The present invention relates to apparatus and methods for determining the density of test materials, and more particularly to an aparatus and method for directly measuring from a composite material comprised of a relatively thin top layer applied to an overlying base material, the density of the top layer.

Nuclear radiation gauges for determining the density of soil and asphaltic materials are well known, as described for example in U.S. Pat. No. 2,781,453. Such gauges employ the phenomenon of Compton scattering of gamma rays and are known by those skilled in the art as "scatter" gauges.

The gauges most commonly used heretofore for measuring the density of soil, asphalt, and other materials are most effective at measuring densities of materials over depths of approximately four to six inches. When the thickness of the test material is at least four to six inches, the prior gauges have been highly successful. However, as the thickness of the test material decreases, increasing difficulty is encountered due to the influence of the underlying material.

With the increasing cost of paving materials, the practice in maintaining and resurfacing paved roadbeds has become one of applying relatively thin overlays, e.g. on the order of about one to two inches, over the existing roadbed. With thin layers of this thickness, prior nuclear density gauges of the type noted above are ineffective for measuring the density of the overlay applied. More particularly, such gauges are not capable of directly measuring the density of layers having a thickness less than about four inches. Because of the depth of penetration of the gamma rays, the gauge "sees" through the thin overlay so that the underlaying pavement substantially influences the gauge reading.

Recognizing this limitation of prior density gauges, efforts were made in the mid 1970's to establish a procedure for determining the density of thin overlays utilizing the then existing gauges. A nomograph was developed which allowed approximation of the density of the thin overlay. However, in order to obtain the density of the overlay by the nomograph technique, it was necessary to know both the density of the underlaying base material and the thickness of the overlay. The technique was as follows. First, the operator determined the density of the base material by taking nuclear density tests of the existing roadbed. Second, after the overlay pavement was applied and compacted, the overlay thickness was determined by taking a core sample, or similar operation. Third, density tests were performed on top of the overlay. With the density measurement from the first test, the overlay thickness measurement and the density data from the second test, the density of the overlay could be approximated by reference to the nomograph.

A similar technique for determining the density of a thin overlay is described in U.S. Pat. No. 4,389,136. As in the nomograph technique, it is necessary to first determine the density of the base prior to application of the overlay, and thereafter to determine the thickness of the overlay and the density of the composite material.

A significant drawback of both the prior art nomograph technique and the technique described in the above-referenced U.S. Pat. No. 4,389,136 is that the underlying pavement may be further compacted when the overlay is compacted, thereby introducing an inconsistency between the gauge reading of the underlying pavement density and its actual density after application of the overlay. Furthermore, it has proven difficult to take the second density reading (after the overlay is applied) at precisely the same location as the first reading. Also, the thickness of the overlay may vary between the sample location and the location where the nuclear gauge is placed for testing. In addition to the above problems, and perhaps more importantly, these techniques require multiple steps, performed both before and after application of the overlay, and usually also require a destructive thickness measurement of the overlay.

Recognizing the shortcomings of the prior methods, a method and apparatus is described in commonlyowned copending U.S. patent application Ser. No. 477,820 filed Mar. 22, 1983, now U.S. Pat. No. 4,525,854, by which the density of a thin overlay may be directly determined. In one aspect, this apparatus comprises a radiation source for emitting radiation into a relatively thin material and any underlying substrate material that is present, and detector means designed for obtaining separate and distinct measurements of scattered radiation at a plurality of detector locations. Because of the design, the separate and distinct radiation measurements are weighted toward the physical characteristics as they exist at different depths in the thin material and underlying substrate and provide independent data that, when interrelated with derived mathematical relationships, serve collectively to determine values for the physical characteristics of the thin layer and substrate.

In the preferred embodiment illustrated in this copending application, the gauge includes a source of gamma radiation and three radiation detectors that provide three independent total radiation counts. The three independently derived total radiation counts, when substituted into three empirically derived simultaneous mathematical equations (each having three unknowns), enable all three unknowns to be calculated. The apparatus may include a microprocessor that incorporates a fixed set of instructions for performing the solution of the three simultaneous equations.

While the techniques described in the aboverefe-renced copending application have been successfully employed for obtaining direct measurement of density of a thin layer of test material, the use of three detectors and the solving of simultaneous equations impose limitations on the cost and efficiency of the gauges employing these techniques.

The present invention represents an improvement over the techniques described in the aforementioned copending application in that a simplified and more economical means and method are employed for achieving direct measurement of the density of a thin overlay.

SUMMARY OF THE INVENTION

In accordance with the present invention, a technique is provided whereby a direct measurement of the density of the thin overlay material is obtained from only two independent density readings performed at the surface of the top layer of the material.

More particularly, the present invention provides a nuclear radiation backscatter gauge for directly measuring from a composite material comprised of a relatively thin top layer of material applied over an underlying base material, the density $D_T$ of the top layer of material. The backscatter gauge comprises:

means for emitting nuclear radiation from a source into the thin layer and the underlying base material and for detecting radiation which is scattered therefrom at two geometrically differing source-to-detector relationships;

signal processing circuit means for responding to the detected scattered radiation at said two source-to-detector relationships and generating respective signals $D_{G1}$ and $D_{G2}$ representatives of the composite densities of the top layer and base layer as measured at the respective source-to-detector relationships, and signal calculating circuit means connected with said signal processing circuit means and operable for determining the density $D_T$ of the top layer from the relationship $$D_T = \frac{k_2 D_{G1} - k_1 D_{G2}}{k_2 - k_1},$$

where $k_1$ and $k_2$ are empirically derived instrument constants.

The instrument constants $k_1$ and $k_2$ which are used in accordance with this technique are functionally related to the thickness X of the top layer. The gauge includes input means for accepting operator input of the approximate thickness X of the top layer and means for providing to said signal calculating circuit means values for the constants $k_1$ and $k_2$ as a function of the thickness X received by said input means.

Although the constants $k_1$ and $k_2$ are functions of the thickness X of the thin layer, the constants are not unduly sensitive to the accuracy of the thickness X. Consequently, it is possible to use an approximation of the thickness and to still achieve an acceptable level of accuracy for many applications. Thus, it is not necessary to take a core sample or to make other destructive thickness measurement of the top layer.

BRIEF DESCRIPTION OF THE DRAWINGS

The invention will be more fully understood from the detailed description which follows, when taken in connection with the accompanying drawings, in which.

DESCRIPTION OF THE ILLUSTRATED EMBODIMENT

While the present invention will be described hereinafter with particular reference to the accompanying drawings, it is to be understood at the outset that it is contemplated that the present invention may be varied in specific detail from that illustrated and described herein while still achieving the desirable characteristics and features of the present invention. Accordingly, the description which follows is intended to be understood as a broad enabling disclosure directed to persons skilled in the applicable arts, and is not to be understood as restrictive.

Figure 1:
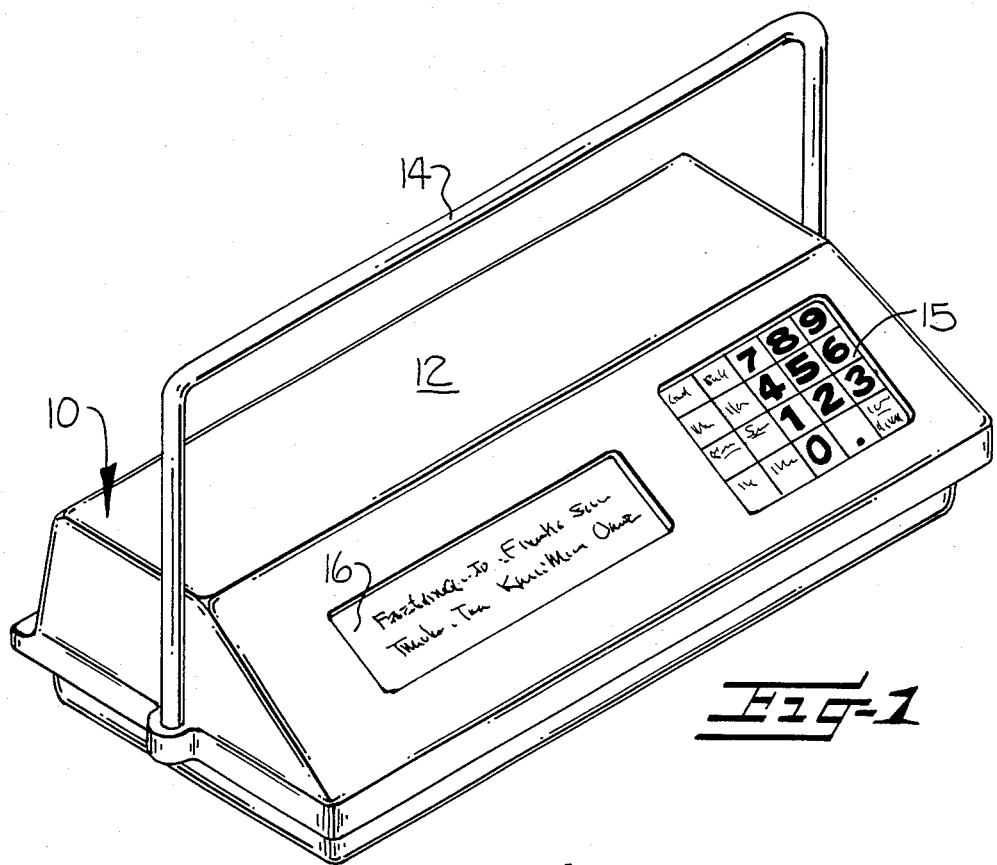
FIG. 1 is a perspective view of a radiation gauge constructed in accordance with the present invention.

Referring now more particularly to the drawings, there is shown in FIG. 1 a radiation gauge 10 constructed in accordance with the invention. The gauge 10 includes a housing, indicated at 12, a handle 14, a keyboard 15, and a display 16. The housing 12 encloses a suitable radiation source 20 (shown in FIG. 2) and two longitudinally spaced apart detector means 22 and 24. The radiation source may be a CS-137 source of gamma radiation and the detector means may take the form of Geiger-Mueller tubes sensitive to photons. As illustrated, the source 20 is located adjacent one end of the base 28 of the housing, and the detector means 22 and 24 are mounted to the base 28 at different longitudinal distances from the source so as to form two geometrically different source-to-detector relationships. A shielding 30 is provided around the source 20 and around the detectors 22 and 24, as is conventional, to prevent radiation from reaching the detectors in a direct path from the source. Additionally, means (not shown) is provided for completely shielding the radiation source when the gauge is not being used for measurement.

Figure 2:
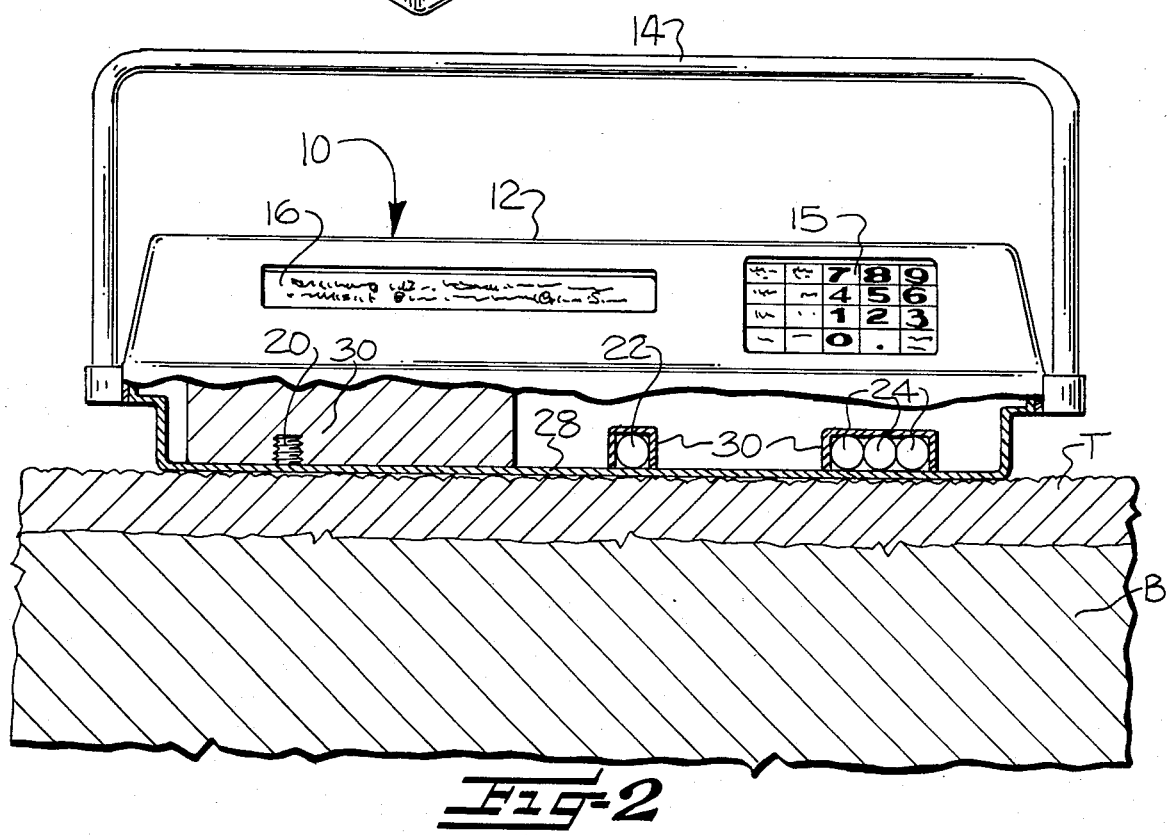
FIG. 2 is a cross sectional view through the lower portion of the gauge, with the gauge resting upon a composite test material including a thin top layer applied over an underlying base material.

As shown in FIG. 2, the gauge 10 is positioned on an asphalt pavement surface comprised of a thin top layer T applied as an overlay over a base material B. The source 20 directs gamma radiation downwardly into the thin top layer t and the underlying base B, and the two detector systems 22, 24 detect radiation which is scattered back to the surface where the detector systems are located.

Prior to further discussion of the structure and operation of gauge 10, it will be helpful to review some of the underlying principles of nuclear density gauge operation and geometry, particularly as applied to multiple layer test materials.

As mentioned earlier, prior nuclear density gauges optimally measure densities over a depth range of approximately 4 to 6 inches. The usual application of these gauges is with single layer, substantially homogeneous materials having a thickness of 4 inches or more. It has been determined that with layers of less than about 4 inches, the gauge "sees" through the top layer and the gauge density reading $D_G$ is significantly influenced by the density $D_B$ of the underlying base material.

Thus, as recognized in commonly-owned copending patent application Ser. No. 477,820 filed Mar. 22, 1983, the gauge density reading $D_G$ is essentially a function of three variables: the density of the top layer ($D_T$), the density of the underlying base ($D_B$), and the thickness of the top layer (X), and may be expressed by the general function:

$$D_G = f(D_T, X, D_B)$$

One specific form of equation which the above general relationship may take is as follows:

$$D_G = (D_B - D_T)k + D_T$$

where the parameter k is a function of X and the particular gauge geometry and characteristics.

It has been determined that the geometrical relationship between a radiation source and a detector has a significant impact on what is seen by the detector. While the geometrical relationship may be varied by changing the angular relationship of the radiation beam with respect to the detector, or by other changes, the geometrical relationship may be varied most conveniently by changing the distance between the source and the detector. This can be accomplished with a single source and single detector system, two sources and a single detector, or as in the embodiment illustrated herein, with a single source and two detector systems which are mounted at different distances from the source. What has been found is that the amount of radiation reaching the detector decreases exponentially with increase in the source to detector distance. Further, as source to detector distance decreases, the reading of the gauge is more heavily weighted toward the density of the material close to the surface. Conversely, at larger source to detector distances, the gauge reading becomes more an average density over the approximately 4 inch depth seen by the gauge. This phenomenon enables detectors placed at different distances from the source to make separate and distinct radiation measurements that are independent of each other. These independent radiation measurements reflect physical characteristics of the same material, but are weighted more heavily toward different depth strata within the material.

Thus, when measurements are made of the same composite material using two detector systems providing two geometrically differing source to detector relationships, the equations for the two detector systems are as follows:

$$D_{G1} = (D_B - D_T)k_1 + D_T$$

$$D_{G2} = (D_B - D_T)k_2 + D_T$$

Solving for $D_T$, the equations above may be expressed as follows:

$$D_T = \frac{k_2 D_{G1} - k_1 D_{G2}}{k_2 - k_1}$$

It will thus be seen that from this equation, it is possible to directly determine the density $D_T$ of the top layer based upon two separate and independent gauge density readings $D_{G1}$ and $D_{G2}$, if values for the constants $k_1$ and $k_2$ for use in the above equation can be determined. The present invention provides a simplified approach to solving the above equation which provide values for $k_1$ and $k_2$ which are applicable to a range of base and top layer density conditions and thicknesses broad enough to cover those normally encountered in the field.

Using metal blocks of two known and different densities which lie at the upper and lower ends of the range of densities normally encountered in field applications, values for $k_{11}$, for the first detector system are empirically determined for different thicknesses X from the equation $$k_{11} = \frac{D_{G1} - D_T}{D_B - D_T}$$

Figure 4:
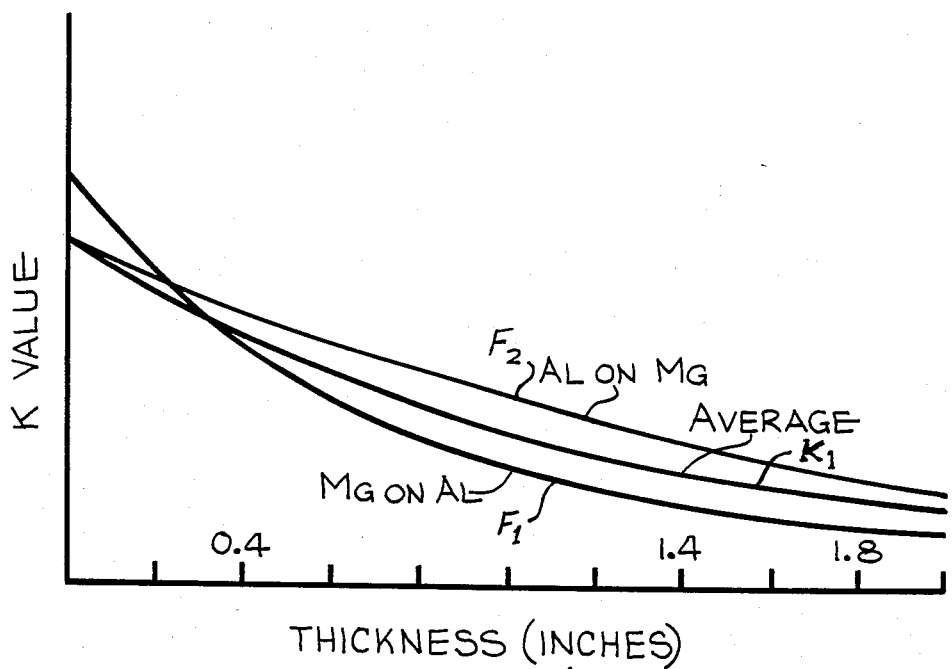
FIG. 4 is a graph illustrating how the instrument constants are derived.

This produces one set of $k_{11}$ data ($F_1$) when the more dense block is located over the less dense block, and a second set of $k_{11}$ data ($F_2$) when the blocks are reversed. For example, using magnesium blocks (density=110 pcf) of various thicknesses ranging from one inch to two inches over an aluminum block (density=169 pcf), a set of points is obtained which, when plotted, defined an exponential curve $F_1$ as shown in FIG. 4. A similar set of measurements using an aluminum block of varying thickness over a magnesium block produces the exponential curve $F_2$ shown in FIG. 4.

The assumption is made that the top and base layer densities $D_T$ and $D_B$ in a field application are somewhere between these two extremes. The arithmethic mean of these curves $F_1$ and $F_2$ yields the curve $k_1$ shown in FIG. 4.

By a similar procedure, values for $k_{21}$ for the second detector system can be empirically determined from the relationship $$k_{21} = \frac{D_{G2} - D_T}{D_B - D_T}$$

and through the use of blocks of known density, similar valus for $F_2$, $F_1$ and $k_2$ can be determined.

It has been determined in accordance with the present invention that the use of these empirically determined average values for $k_1$ and $k_2$ for a given thickness X in the equation $$D_T = \frac{k_2 D_{G1} - k_1 D_{G2}}{k_2 - k_1}$$

produces a top layer density measurement of acceptable accuracy for most field applications.

In applying the above principles to the density gauge of this invention, it thus is possible to use fixed values for $k_1$ and $k_2$ which are applicable over a fairly broad practical working range of thickness and density conditions. This may be built into suitable digital or analog computation means for thereby automatically generating a value $D_T$ from the readings $D_{G1}$ and $D_{G2}$ obtained from the two detector means.

For even greater accuracy, it is desirable to take into account the effect of the top layer thickness X on the values for $k_1$ and $k_2$. Equations may be fitted to the curves $k_1$ and $k_2$ which define $k_1$ and $k_2$ as a function of thickness X. Since, as seen above, the $k_1$ and $k_2$ curves are not unduly sensitive to variations in thickness X over a limited range, the operator may simply supply an approximate value for the top layer thickness X, and the computation means may be programmed to generate values for $k_1$ and $k_2$ as a function of the X value entered, which will provide sufficient accuracy for many applications.

Figure 3:
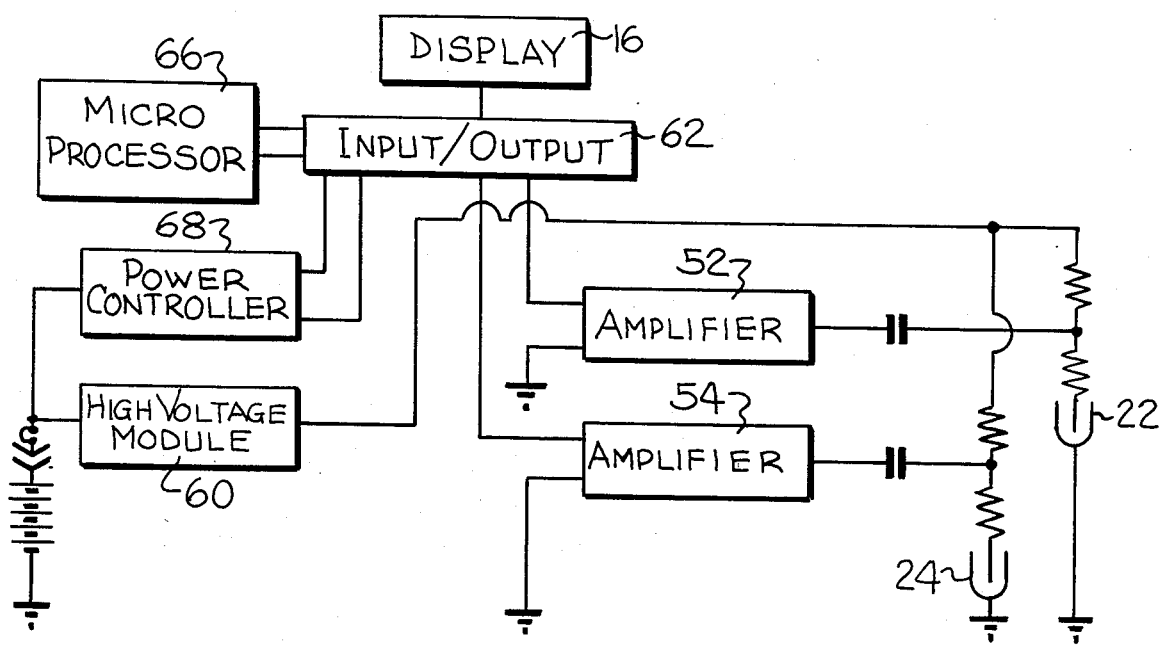
FIG. 3 is a schematic diagram of certain circuit components of the gauge.

Referring now to FIG. 3, each of the detectors 22 and 24 is electrically connected with a corresponding amplifier 52, 54. Additionally, as is required, the detectors are connected with a source 60 of high voltage. Outputs from the amplifiers 52 and 54 are directed to an input-/output circuit generally indicated at 62 and are available through such circuitry to an electronic computing device shown in the form of a microprocessor 66 and to display 16. Power to the entire device is supplied by a power controller 68.

The microprocessor performs in the circuit of the present invention (as schematically illustrated in FIG. 3) a number of functions including governing time intervals for gauging in both "standard" and "measure" modes. The microprocessor also serves the function of a recorder operatively associated with the detectors for separately recording the measured radiation information from each detector. In this regard, the radiation information preferably takes the form of a total radiation count for each Geiger-Mueller detector per time interval. In other embodiments the radiation information may take other forms, such as radiation count rates.

The microprocessor also serves to store, in appropriate form, the instructions needed for converting the amplified radiation counts from detector means 22, 24 into values for $D_{G1}$ and $D_{G2}$, and for employing the abovenoted equation (or an equivalent form) to arrive at a value for $D_T$. Other functions, generally known to persons appropriately skilled in the art, are performed by the microprocessor.

With reference to FIG. 3, in operation the apparatus 10 may be initially placed in the "standard" mode to take a standard count on a reference standard in the manner well known to those skilled in the art. Once the standard count information is stored in the microprocessor 66, the gauge may be placed in the "measure" mode for measuring the density of an appropriate test material, for example resurfaced pavement including a thin overlay and an underlying pavement base. Through an appropriate set of instructions stored in the microprocessor 66, the operator will first be prompted (through an information displayed on display 16) to enter into the keyboard 15 the desired time interval over which the radiation counts will be taken. The operator will then be prompted to enter the presumed or approximate thickness of the thin top layer. Now the gauge is ready to determine the density of the selected thickness. Pressing an appropriate key on the keyboard (e.g. "START"), will initiate the reading procedure. At the end of the selected time interval, the total counts detected by the detector systems will be used to calculate the density $D_T$ of the top layer, using the relationships described earlier herein, and the results will be displayed on the display 16.

That which is claimed is:

1. A nuclear radiation backscatter gauge for directly measuring from a composite material comprised of a relatively thin top layer of material applied over an underlying base material, the density $D_T$ of the top layer, comprising means for emitting nuclear radiation from a source into the relatively thin top layer of material and the underlying base material and for detecting radiation which is scattered therefrom at two geometrically differing source-to-detector relationships;

signal processing circuit means for responding to the detected scattered radiation at said two source-to-detector relationships and generating respective signals $D_{G1}$ and $D_{G2}$ representative of the composite densities of the top layer and base layer as measured at the respective source-to-detector relationships, and signal calculating circuit means connected with said signal processing circuit means and operable for determining the density $D_T$ of the top layer from the relationship $$D_T = \frac{k_2 D_{G1} - k_1 D_{G2}}{k_2 - k_1},$$

where $k_2$ and $k_1$ are empirically derived instrument constants.

2. A nuclear radiation backscatter gauge for directly measuring from a composite material comprised of a relatively thin top layer of material applied over an underlying base material, the density $D_T$ of the top layer, comprising nuclear radiation source means for directing radiation into the thin layer and the underlying base material;

two nuclear radiation detector means so positioned with respect to said source as to form two geometrically differing source-to-detector relationships;

signal processing circuit means operatively connected with each of said detector means for responding to detected radiation and generating respective signals $D_{G1}$ and $D_{G2}$ representative of the composite densities of the top layer and base layer as measured by the respective detector means; and signal calculating circuit means connected with said signal processing circuit means and operable for determining the density $D_T$ of the top layer from the relationship $$D_T = \frac{k_2 D_{G1} - k_1 D_{G2}}{k_2 - k_1},$$

where $k_1$ and $k_2$ are empirically derived instrument constants.

3. A nuclear radiation gauge according to claim 2 wherein the constants $k_1$ and $k_2$ are functionally related to the thickness X of the top layer, and said gauge includes input means for accepting operator input of the approximate thickness X of the top layer and means for providing to said signal calculating circuit means values for the constants $k_1$ and $k_2$ as a function of thickness X received by said input means.

4. A nuclear radiation gauge according to claim 2 including display means for displaying the value for $D_T$ obtained by said signal calculating circuit means.

5. A nuclear radiation density measurement method for directly measuring from a composite material comprised of a relatively thin top layer applied over an underlying base material, the density $D_T$ of the top layer, comprising the steps of:

directing nuclear radiation from a source into the thin material and the underlying base material;

detecting radiation which is scattered therefrom at two geometrically differing source-to-detector relationships and determining therefrom the composite densities $D_{G1}$ and $D_{G2}$ of the composite material as measured at the respective source-to-detector relationships; and determining the density $D_T$ of the top layer from the relationship $$D_T = \frac{k_2 D_{G1} - k_1 D_{G2}}{k_2 - k_1},$$

where $k_1$ and $k_2$ are empirically derived instrument constants.

6. A nuclear radiation density measurement method for directly measuring from a composite material comprised of a relatively thin top layer applied over an underlying base material, the density $D_T$ of the top layer, comprising the steps of:

positioning at the surface of the top layer a nuclear backscatter density gauge having a nuclear radiation source and two nuclear radiation detector means so positioned with respect to the source as to form two geometrically differing source-to-detector relationships;

detecting backscattered radiation at the two detector means and determining therefrom the composite densities $D_{G1}$ and $D_{G2}$ of the composite material as measured by the two detector means; and determining the density $D_T$ of the top layer from the relationship $$D_T = \frac{k_2 D_{G1} - k_1 D_{G2}}{k_2 - k_1},$$

where $k_1$ and $k_2$ are empirically derived instrument constants.

7. A nuclear radiation density measurement method for directly measuring from a composite material comprised of a relatively thin top layer applied over an underlying base material, the density $D_T$ of the top layer, comprising the steps of:

positioning at the surface of the top layer a nuclear backscatter density gauge having a nuclear radiation source and two nuclear radiation detector means so positioned with respect to the source as to form two geometrically differing source-to-detector relationships;

detecting backscattered radiation at the two detector means and determining therefrom the composite densities $D_{G1}$ and $D_{G2}$ of the top layer and base layer as measured by the two detector means; and providing to the gauge the approximate thickness X of the top layer and calculating therefrom values for instrument constants $k_1$ and $k_2$, said constants being empirically derived instrument constants which are functionally related to the thickness X, and determining the density $D_T$ of the top layer from the relationship $$D_T = \frac{k_2 D_{G1} - k_1 D_{G2}}{k_2 - k_1}.$$

* * * * *